US011931395B2

(12) United States Patent
Carle et al.

(10) Patent No.: US 11,931,395 B2
(45) Date of Patent: *Mar. 19, 2024

(54) TOPICAL SKIN COMPOSITIONS FOR TREATING ROSACEA AND SKIN REDNESS

(71) Applicant: MARY KAY INC., Addison, TX (US)

(72) Inventors: Tiffany Carle, Dallas, TX (US); David Gan, Southlake, TX (US); Geetha Kalahasti, Plano, TX (US)

(73) Assignee: MARY KAY INC., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/100,763

(22) Filed: Jan. 24, 2023

(65) Prior Publication Data

US 2023/0321176 A1  Oct. 12, 2023

Related U.S. Application Data

(63) Continuation of application No. 17/374,549, filed on Jul. 13, 2021, now Pat. No. 11,590,194, which is a continuation of application No. 16/792,751, filed on Feb. 17, 2020, now Pat. No. 11,090,352.

(60) Provisional application No. 62/807,141, filed on Feb. 18, 2019.

(51) Int. Cl.
A61K 36/889 (2006.01)
A61K 8/92 (2006.01)
A61K 8/9789 (2017.01)
A61K 8/9794 (2017.01)
A61K 8/99 (2017.01)
A61K 9/06 (2006.01)
A61K 9/107 (2006.01)
A61K 35/74 (2015.01)
A61K 36/185 (2006.01)
A61K 36/61 (2006.01)
A61P 17/04 (2006.01)
A61Q 19/00 (2006.01)
A61Q 19/08 (2006.01)

(52) U.S. Cl.
CPC ............ A61K 36/889 (2013.01); A61K 8/922 (2013.01); A61K 8/9789 (2017.08); A61K 8/9794 (2017.08); A61K 8/99 (2013.01); A61K 9/06 (2013.01); A61K 9/107 (2013.01); A61K 35/74 (2013.01); A61K 36/185 (2013.01); A61K 36/61 (2013.01); A61P 17/04 (2018.01); A61Q 19/007 (2013.01); A61Q 19/08 (2013.01)

(58) Field of Classification Search
None
See application file for complete search history.

(56) References Cited

U.S. PATENT DOCUMENTS

| | | | |
|---|---|---|---|
| 5,972,993 | A | 10/1999 | Ptchelintsev |
| 8,535,738 | B2 | 9/2013 | Collins et al. |
| 9,060,924 | B2 | 6/2015 | Tawashi et al. |
| 9,375,462 | B1 | 6/2016 | VanderVeer |
| 9,687,517 | B2 | 6/2017 | Collins et al. |
| 10,543,158 | B2 | 1/2020 | Graban et al. |
| 2004/0081714 | A1 | 4/2004 | Pauly et al. |
| 2005/0238613 | A1 | 10/2005 | Cals-Grierson et al. |
| 2006/0198800 | A1 | 9/2006 | Dilallo et al. |
| 2015/0011489 | A1 | 1/2015 | Jacovella |
| 2017/0020808 | A1 | 1/2017 | Florence et al. |
| 2018/0071547 | A1 | 3/2018 | Decaux et al. |
| 2019/0038689 | A1 | 2/2019 | Kalahasti et al. |

FOREIGN PATENT DOCUMENTS

| | | |
|---|---|---|
| KR | 10-2016-0068310 | 6/2016 |
| WO | WO 2017/180440 | 10/2017 |
| WO | WO 2017/192110 | 11/2017 |
| WO | WO 2017/197396 | 11/2017 |
| WO | WO 2017/204617 | 11/2017 |
| WO | WO 2018/004490 | 1/2018 |
| WO | WO 2018/056936 | 3/2018 |

OTHER PUBLICATIONS

"Corneotherapy." Jan. 24, 2016 and California SCC, Barnet.
"Epidermist 4.0: New Skin Builder." Cosmetics Business, Jul. 22, 2013, https://www.cosmeticsbusiness.com/news/article_page/EPIDERMIST_40_New_Skin_Builder/89190. Accessed Oct. 8, 2021.
Ardekani et al., "Comparison of Antioxidant Activity and Total Phenol Contents of some Date Seed Varieties from Iran" Iranian Journal of Pharmaceutical Research 2010, 9(2), 141-146.
Benoiderm Efficacy Report. Technical Dossier 12-073GB Oct. 2012, 46 pages.
Cole, Gary W., "Rosacea" MedicineNet, https://www.medicinenet.com/rosacea/article.htm#rosacea_facts. Accessed Apr. 8, 2020.
Galderma. "About Soolantra Cream" Soolantra, https://www.soolantra.com/about-rosacea-treatment. Accessed Apr. 8, 2020.
Gollnick et al., "Azelaic acid 15% gel in the treatment of rosacea" Expert Opin Pharmacother. 2008, 9(15), 2699-2706.
International Search Report and Written Opinion issued in corresponding PCT application No. PCT/US2020/018520, dated May 25, 2020.
Kwape et al., "Antioxidant and antidiabetic potential of Myrothamnus flabellifolius found in Botswana" Cogent Biology 2016, 2(1), 11 pages.
Lam et al., "Can the tea tree oil (Australian native plant: Melaleuca alternifolia Cheel) be an alternative treatment for human demodicosis on skin?" Parasitology 2018, 145(12), 1510-1520.
Pazyar et al., "A review of applications of tea tree oil in dermatology" International Journal of Dermatology 2013, 52(7), 784-790.
Tighe et al., "Terpinen-4-ol is the most active ingredient of tea tree oil to kill Demodex mites" Translational Vision Science & Technology 2013, 2(7), 1-8.

Primary Examiner — Michael V Meller
(74) Attorney, Agent, or Firm — NORTON ROSE FULBRIGHT US LLP

(57) ABSTRACT

A method of topically applying to skin a composition comprising a water soluble Phoenix dactylifera seed extract, an essential oil from the leaves of tea tree, an aqueous Myrothamnus flabellifolia leaf and stem extract, and a saccharide isomerate comprising an exopolysaccharide of Vibrio alginolyticus is disclosed.

19 Claims, No Drawings

TOPICAL SKIN COMPOSITIONS FOR TREATING ROSACEA AND SKIN REDNESS

CROSS-REFERENCE TO RELATED APPLICATIONS

This application is a continuation of U.S. patent application Ser. No. 17/374,549 filed Jul. 13, 2021, which is a continuation of U.S. patent application Ser. No. 16/792,751 filed Feb. 17, 2020 (now U.S. Pat. No. 11,090,352), which claims the benefit of priority to U.S. Provisional Patent Application No. 62/807,141 filed Feb. 18, 2019. The contents of each application is hereby incorporated into the present application by reference.

BACKGROUND OF THE INVENTION

A. Field of the Invention

The present invention relates generally to topical skin care compositions that can reduce rosacea, erythema, and/or skin inflammation, and inhibit nitric oxide synthase. The combination of ingredients can include *Phoenix dactylifera* extract, tea tree oil, *Myrothamnus flabellifolia* extract, and saccharide isomerate.

B. Description of Related Art+

Rosacea is a common skin condition that affects millions of individuals and negatively impacts their quality of life. In the United States alone, it is estimated that nearly 14 million people are living with rosacea. Women over the age of 30 having fair skin, particularly sun-damaged skin, are more likely to develop rosacea. Other risk factors include smoking, a family history of rosacea, and Celtic or Scandinavian ancestry. Although women are more likely to develop rosacea, men are more likely to develop more severe cases of the condition.

Rosacea causes redness and visible blood vessels in a person's face, commonly affecting the central third of a person's face and particularly the nose, and with varying intensity of redness over time. One of four subtypes of rosacea includes erythematotelangiectatic rosacea, characterized by redness, flushing, and visible blood vessels. The characteristic facial redness associated with this type can persist in a person's face, with the small blood vessels of the nose and cheeks swelling and becoming more visible during flare-ups. Papulopustular rosacea, a second subtype, is characterized by redness, swelling, and acne-like breakouts. In some cases, the swollen red bumps and pimples can also contain pus and may feel tender or hot to the touch. A third subtype is phymatous rosacea, which is characterized by skin thickening and bumpy skin texture and in more severe cases can cause rhinophyma, a thickening of the skin on the nose causing the nose to appear bulbous. Ocular rosacea, the fourth and most severe type of rosacea, affects a person's eyes and causes dryness, irritation, swollen and reddened eyelids, and the appearance of bumps that look like a sty.

While the underlying etiology of rosacea is unknown, the basic process involves dilation of the small blood vessels in the face. Rosacea patients typically have a genetically mediated reduction in the ability to dampen facial inflammation that can be incited by environmental factors such as sunburn, demodicosis (*Demodex folliculorum* in the hair follicles), flushing, and certain medications. Rosacea tends to affect the "blush" areas of the face and is more common in people who are predisposed to flushing easily. Additionally, a variety of triggers are known to aggravate rosacea symptoms. These include emotional factors (e.g., stress, fear, anxiety, embarrassment, emotional upsets, etc.) as well as environmental factors (e.g., strong winds, change in the humidity, sun exposure, and sun-damaged skin). Exercise, alcohol consumption, smoking, and spicy foods are other well-known triggers that can aggravate rosacea by increasing blood flow to the surface of the skin.

Others have attempted to create compositions and methods that reduce rosacea, skin inflammation and erythema. Some have attempted to address multiple pathways involved in skin inflammation all at once by using multiple active ingredients in a single composition. For example, U.S. Pat. Nos. 8,535,738 and 9,687,517 teach several pathways that may be involved in inflammation and provides lists of ingredients that may address some of these pathways. However, only a few combinations of actives were actually tested for compatibility and effectiveness. It is unclear if other combinations of the ingredients therein are effective, may cause undesired side effects, or may exacerbate the problems associated with skin inflammation.

Treatments for rosacea have also included the use of antibiotics such as tetracyclines, clindamycin, erythromycin, and ivermectin (e.g., SOOLANTRA® Cream 1%). See, e.g., U.S. Pat. No. 5,972,993 and U.S. Publication No. 2015/0011489. As an alternative, METROGEL® (metronidazole 0.75% gel) has been used as a topical composition with limited effectiveness on treating papules and pustules associated with rosacea, but has been ineffective in reducing skin redness, telangiectases, or flushing. See, e.g., U.S. Pat. No. 5,972,993. More recently, the use of azelaic acid (e.g., FINACEA® 15% gel, AZELEX® 20% cream) has shown promise in treating mild to moderate papules and pustules through an anti-inflammatory effect by reducing reactive oxygen species. See Cole, Gary W., *Rosacea*, MedicineNet (Jan. 4, 2019), https://www.medicinenet.com/rosacea/article.htm#rosacea_facts and Gollnick H. and Layton, A. (2008), Azelaic acid 15% gel in the treatment of rosacea, *Expert Opinion on Pharmacotherapy*, 9(15), 2699-2706. DOI: 10.1517/14656566.9.15.2699. Further, the anti-parasitic and anti-inflammatory properties of ivermectin have reportedly been effective in treating bumps, but the exact mechanism of action of ivermectin, and its long term effects, are still unknown. Galderma, *Soolantra* (Jan. 4, 2019), https://www.soolantra.com/about-rosacea-treatment.

Drying lotions have also been used, but these are aesthetically unappealing as they can contain about 2% to 5% sulfur, which leaves an unpleasant smell. U.S. Pat. No. 5,972,993 teaches a topical composition to treat rosacea that contains antioxidants selected from a group that includes sulfur-containing compounds. Although imidazole drugs (e.g., ketoconazole) have been shown to be useful in treating rosacea, the safety of the continuous long-term use of potent antimicrobial, antifungal, and antibacterial agents is unknown and may cause resistance. In more severe cases of rosacea, corticosteroid drugs and retinoids (e.g., isotretinoin) have been used, but these drugs carry an even greater risk of unwanted side effects than antibiotics, thus limiting their prolonged use.

Demodicosis, or the uncontrolled infestation of *Demodex* mites (*Demodex folliculorum* and *Demodex brevis*), a common ectoparasite that infests the pilosebaceous unit of the skin, has been implicated in several skin diseases including rosacea as a cause of papulopustular skin lesions and perifollicular inflammatory infiltrate. Once demodicosis affects the face, it tends to spread and flourish in the eyelids because the periorbital area of the skin is not as accessible to daily hygiene due to surrounding protruding body parts such as the nose, the brow, and the cheek regions. The prevalence of *Demodex* mites increases with age and is observed in 84% to 100% of the population between 60 to 70 years of age. Tea tree oil (1% terpinen-4-ol) has been shown to have an acaricidic effect on *Demodex* mites. Tighe, et al. (2013), Terpinen-4-ol is the most active ingredient of tea tree oil to kill *Demodex* mites, *Translational Vision Science & Technology*, 2(7), 1-8. DOI: 10.1167/tvst.2.7.2.

Of these attempts to treat rosacea, many have been ineffective, only addressed one or a few of the undesired outcomes of rosacea, inflammation, and erythema, or cause unacceptable side effects themselves, such as skin irritation or an allergic response. Further, not every effective composition is compatible with every skin type. Thus, there is a need for new products that are effective at reducing rosacea, erythema, and skin inflammation.

SUMMARY OF THE INVENTION

The inventors have identified a solution to at least some of the problems associated with rosacea, erythema, and/or skin inflammation. The solution resides in a combination of ingredients that can include *Phoenix dactylifera* extract, tea tree oil, *Myrothamnus flabellifolia* extract, and saccharide isomerate. The combination can be used to create topical compositions that are effective at reducing rosacea, erythema, and/or skin inflammation, and reducing nitric oxide synthase activity. In some instances, *Phoenix dactylifera* extract was shown to increase α2A adrenergic receptor agonist activity, reduce oxidation, increase a composition's or skin's anti-oxidant capacity, inhibit production of cyclooxygenase-2 (COX-2), vascular endothelial growth factor (VEGF), interleukin-6 (IL-6), interleukin-8 (IL-8), and tumor necrosis factor alpha (TNF-α), increase collagen stimulation and lysyl oxidase expression, and inhibit matrix metalloproteinase 1 (MMP1) activity. In some instances, saccharide isomerate was shown to reduce tumor necrosis factor alpha (TNF-α) production, inhibit nitric oxide synthase, increase occludin and filaggrin production, and increase skin moisturization. In some specific instances, *Myrothamnus flabellifolia* extract was shown to reduce TNF-α production and inhibit nitric oxide synthase. In some instances, the extracts can be aqueous extracts. In some instances, other solvents such as alcohols, glycols, hydroalcoholic, and/or hydroglycolic extracts can be used.

In some aspects, there is disclosed a topical composition. In some aspects, the topical composition includes any one of, any combination of, or all of *Phoenix dactylifera* extract, tea tree oil, *Myrothamnus flabellifolia* extract, and saccharide isomerate. In some instances, the topical composition includes an effective amount of *Phoenix dactylifera* extract, tea tree oil, *Myrothamnus flabellifolia* extract, and saccharide isomerate to reduce rosacea, erythema, and/or inflammation. In some instances, the topical composition includes an effective amount of *Phoenix dactylifera* extract, tea tree oil, *Myrothamnus flabellifolia* extract, and saccharide isomerate to reduce transient or persistent erythema, telangiectasia, inflammatory papules, pustules, transient flushing of the skin, persistent flushing of the skin, and/or hyperplasia of a connective tissue. In some instances, the topical composition includes an effective amount of *Phoenix dactylifera* extract, tea tree oil, *Myrothamnus flabellifolia* extract, and saccharide isomerate to inhibit nitric oxide synthase, increase α2A adrenergic receptor agonist activity, reduce oxidation, increase a composition's or skin's anti-oxidant capacity, inhibit COX-2 production, inhibit VEGF production, inhibit IL-6 production, inhibit IL-8 production, reduce TNF-α production, increase collagen stimulation, increase lysyl oxidase expression, inhibit MMP1 activity, increase occludin production, increase filaggrin production, and/or increase skin moisturization. In some instances, the topical composition includes an effective amount of *Phoenix dactylifera* extract to increase α2A adrenergic receptor agonist activity, reduce oxidation, increase a composition's or skin's anti-oxidant capacity, inhibit COX-2 production, inhibit VEGF production, inhibit IL-6 production, inhibit IL-8 production, reduce TNF-α production, increase collagen stimulation, increase lysyl oxidase expression, and/or inhibit MMP1 activity. In some instances, the topical composition includes an effective amount of tea tree oil to kill *Demodex folliculorum* and *Demodex brevis*. In some instances, the topical composition includes an effective amount of saccharide isomerate to reduce TNF-α production, inhibit nitric oxide synthase, increase occludin production, increase filaggrin production, and/or increase skin moisturization. In some instances, the topical composition includes an effective amount of *Myrothamnus flabellifolia* extract to reduce TNF-α production and/or inhibit nitric oxide synthase.

In some instances, the topical composition includes water. In some instances, the saccharide isomerate and/or *Myrothamnus flabellifolia* extract is an aqueous extract. By aqueous extract, it is meant that an aqueous solution can be used as the extractant or solvent to obtain the extract. In addition to water, the aqueous solution can, in some instances, include an alcohol(s), a glycol(s), or combinations thereof. The aqueous extracts can be in liquid form or in powdered form. The saccharide isomerate can contain an exopolysaccharide of *Vibrio alginolyticus* belonging to the family of Thalasso plankton. The *Myrothamnus flabellifolia* extract can be an extract of the leaf and stem of *Myrothamnus flabellifolia*. The *Phoenix dactylifera* extract can be a water soluble extract from palm date seeds. The tea tree oil can be an essential oil from the leaves of the tea tree *Melaleuca alternifolia*.

The topical compositions disclosed herein may further comprise one or more ingredients described herein. For example, the composition may comprise one or more additional ingredients selected from one or more conditioning agents, moisturizing agents, pH adjusters, structuring agents, inorganic salts, and preservatives. In some instances, the topical composition further includes water. The amounts of the ingredients within the composition can vary (e.g., amounts can be as low as 0.000001% to as high as 98% w/w or any range therein). In some instances, the topical composition is an emulsion, serum, gel, gel emulsion, or gel serum.

Methods of use for the compositions disclosed herein are also disclosed. In some aspects, a method is disclosed of improving a condition or appearance of skin, comprising applying any one of the compositions disclosed herein to skin in need thereof. In one aspect, any one of the compositions disclosed herein is applied to skin and the composition is left on the skin, or alternatively removed from the skin after a period of time. In some aspects, the compositions disclosed herein are used to treat and/or reduce rosacea. In some aspects, the compositions disclosed herein are used to treat and/or reduce erythema. In some aspects, the compositions disclosed herein are used to treat and/or reduce inflammation. In another aspect, the compositions disclosed herein are used to inhibit or reduce nitric oxide synthase activity. In some aspects, the compositions disclosed herein are used to increase α2A adrenergic receptor agonist activity, reduce oxidation, inhibit COX-2 production, inhibit VEGF production, inhibit IL-6 production, inhibit IL-8 production, reduce TNF-α production, increase collagen stimulation, increase lysyl oxidase expression, inhibit MMP1 activity, to kill *Demodex folliculorum* and/or *Demodex brevis*, inhibit nitric oxide synthase, increase occludin production, increase filaggrin production, and/or increase skin moisturization. In some aspects, the compositions disclosed herein include an effective amount of *Phoenix dactylifera* extract and are used to increase α2A adrenergic receptor agonist activity, reduce oxidation, inhibit COX-2 production, inhibit VEGF production, inhibit IL-6 production, inhibit IL-8 production, reduce TNF-α production, increase collagen stimulation, increase lysyl oxidase expression, and/or inhibit MMP1 activity. In some aspects, the compositions disclosed herein include an effective amount of tea tree oil and are used to kill *Demodex folliculorum* and/or *Demodex brevis*. In some aspects, the compositions disclosed herein include an effective amount of saccharide isomerate and are used to reduce TNF-α production, inhibit nitric oxide synthase, increase occludin production, increase filaggrin production, and/or increase skin moisturization. In some aspects, the compositions disclosed herein include an effective amount of *Myrothamnus flabellifolia* extract and are used to reduce tumor necrosis factor alpha (TNF-α) production and/or inhibit nitric oxide synthase. In some aspects, the methods include applying any one of the topical compositions described herein to skin. In some aspects, the methods include applying the composition to skin of a face. In some instances, the method includes applying the composition to red skin, rosacea skin, erythemic skin, and/or inflamed skin.

In some aspects, the compositions of the present invention are formulated as a topical skin composition. The composition can have a dermatologically acceptable vehicle or carrier for the compounds and extracts. The composition can further include a moisturizing agent or a humectant, a surfactant, a silicone containing compound, a UV agent, an oil, and/or other ingredients identified in this specification or those known in the art. The composition can be a mask, lotion, cream, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben. In some embodiments, the composition is paraben-free.

Compositions of the present invention can have UVA and UVB absorption properties. The compositions can have a sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Kits that include the compositions of the present invention are also contemplated. In certain embodiments, the composition is comprised in a container. The container can be a bottle, dispenser, or package. The container can dispense a pre-determined amount of the composition. In certain aspects, the composition is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute(s). An example of a rinse off composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a foundation, a night cream, a lipstick, a cleanser, a toner, a sunscreen, a mask, an anti-aging product, a deodorant, an antiperspirant, a perfume, a cologne, etc.

Also disclosed are the following Embodiments 1 to 38 of the present invention. Embodiment 1 is a method of treating skin, the method comprising topically applying to the skin an effective amount of a topical composition comprising *Phoenix dactylifera* extract, tea tree oil, *Myrothamnus flabellifolia* extract, and saccharide isomerate wherein the skin is treated. Embodiment 2 is the method of Embodiment 1, wherein the skin is treated to reduce rosacea, erythema and/or inflammation, and wherein the rosacea, erythema, and/or inflammation is reduced. Embodiment 3 is the method of Embodiments 1 to 2, wherein the skin is treated to reduce transient or persistent erythema, telangiectasia, inflammatory papules and/or pustules, transient or persistent flushing of the skin, and/or hyperplasia of a connective tissue. Embodiment 4 is the method of any of Embodiments 1 to 3, wherein the skin is treated to inhibit nitric oxide synthase, increase α2A adrenergic receptor agonist activity, reduce oxidation, increase anti-oxidant capacity of the skin, inhibit cyclooxygenase-2 (COX-2) production, inhibit vascular endothelial growth factor (VEGF) production, inhibit interleukin-6 (IL-6) and interleukin-8 (IL-8) production, reduce tumor necrosis factor alpha (TNF-α) production, increase collagen stimulation, increase lysyl oxidase expression, inhibit matrix metalloproteinase 1 (MMP1) activity, increase occludin production, increase filaggrin production, increase skin moisturization, and wherein nitric oxide synthase is inhibited, α2A adrenergic receptor agonist activity is increased, oxidation is reduced, skin anti-oxidant capacity is increased, COX-2 production is inhibited, VEGF production is inhibited, IL-6 production is inhibited, IL-8 production is inhibited, TNF-α production is inhibited, collagen stimulation is increased, lysyl oxidase expression is increased, MMP1 activity is inhibited, occludin production is increased, filaggrin production is increased, and/or skin moisturization is increased. Embodiment 5 is the method of any of Embodiments 1 to 4, wherein the topical composition further comprises water. Embodiment 6 is the method of any of Embodiments 1 to 5, wherein the saccharide isomerate and/or *Myrothamnus flabellifolia* extract is an aqueous extract. Embodiment 7 is the method of Embodiment 6, wherein the aqueous extracts are in liquid form. Embodiment 8 is the method of Embodiment 6, wherein the aqueous extracts are in powdered form. Embodiment 9 is the method of any of Embodiments 1 to 8, wherein the saccharide isomerate comprises an exopolysaccharide of *Vibrio alginolyticus* belonging to the family of Thalasso plankton. Embodiment 10 is the method of any of Embodiments 1 to 9, wherein the *Myrothamnus flabellifolia* extract is an extract of the leaf and stem of *Myrothamnus flabellifolia*. Embodiment 11 is the method of any of Embodiments 1 to 10, wherein the *Phoenix dactylifera* extract is a water soluble extract from *Phoenix dactylifera* seeds. Embodiment 12 is the method of any of Embodiments 1 to 11, wherein the tea tree oil is an essential oil from the leaves of the tea tree *Melaleuca alternifolia*. Embodiment 13 is the method of any of Embodiments 1 to 12, wherein the topical composition is an emulsion, serum, gel, gel emulsion, or gel serum. Embodiment 14 is the method of any of Embodiments 1 to 13, wherein the topical composition is an oil in water emulsion or a water in oil emulsion. Embodiment 15 is the method of any of Embodiments 1 to 14, wherein the composition is applied to skin of a face. Embodiment 16 is the method of any of Embodiments 1 to 15, wherein the composition comprises an effective amount of *Phoenix dactylifera* extract to increase α2A adrenergic receptor agonist activity, reduce oxidation, increase anti-oxidant capacity of the skin, inhibit cyclooxygenase-2 (COX-2) production, inhibit vascular endothelial growth factor (VEGF) production, inhibit interleukin-6 (IL-6) and interleukin-8 (IL-8) production, reduce tumor necrosis factor alpha (TNF-α) production, increase collagen stimulation, increase lysyl oxidase expression, and/or inhibit matrix metalloproteinase 1 (MMP1) activity. Embodiment 17 is the method of any of Embodiments 1 to 16, wherein the composition comprises an effective amount of tea tree oil to kill *Demodex folliculorum* and *Demodex brevis*. Embodiment 18 is the method of any of Embodiments 1 to 15, wherein the composition comprises an effective amount of saccharide isomerate to reduce tumor necrosis factor alpha (TNF-α) production, inhibit nitric oxide synthase, increase occludin production, increase filaggrin production, and/or increase skin moisturization. Embodiment 19 is the method of any of Embodiments 1 to 15, wherein the composition comprises an effective amount of *Myrothamnus flabellifolia* extract to reduce tumor necrosis factor alpha (TNF-α) production, and/or inhibit nitric oxide synthase. Embodiment 20 is a topical skin composition comprising *Phoenix dactylifera* extract, tea tree oil, *Myrothamnus flabellifolia* extract, and saccharide isomerate. Embodiment 21 is the composition of Embodiment of 20, wherein the topical composition comprises an effective amount of *Phoenix dactylifera* extract, tea tree oil, *Myrothamnus flabellifolia* extract, and saccharide isomerate to reduce rosacea, erythema, and/or inflammation. Embodiment 22 is the composition of Embodiments 20 to 21, wherein the topical composition comprises an effective amount of *Phoenix dactylifera* extract, tea tree oil, *Myrothamnus flabellifolia* extract, and saccharide isomerate to reduce transient or persistent erythema, telangiectasia, inflammatory papules and/or pustules, transient or persistent flushing of the skin, and/or hyperplasia of a connective tissue. Embodiment 23 is the composition of any of Embodiments 20 to 22, wherein the topical composition comprises an effective amount of *Phoenix dactylifera* extract, tea tree oil, *Myrothamnus flabellifolia* extract, and saccharide isomerate to inhibit nitric oxide synthase, increase α2A adrenergic receptor agonist activity, reduce oxidation, increase anti-oxidant capacity of the composition or of skin, inhibit cyclooxygenase-2 (COX-2) production, inhibit vascular endothelial growth factor (VEGF) production, inhibit interleukin-6 (IL-6) and interleukin-8 (IL-8) production, reduce tumor necrosis factor alpha (TNF-α) production, increase collagen stimulation, increase lysyl oxidase expression, inhibit matrix metalloproteinase 1 (MMP1) activity, increase occludin production, increase filaggrin production, and/or increase skin moisturization. Embodiment 24 is the composition of any of Embodiments 20 to 23, wherein the saccharide isomerate and/or *Myrothamnus flabellifolia* extract is an aqueous extract. Embodiment 25 is the topical composition of Embodiment 24, wherein the aqueous extracts are in liquid form. Embodiment 26 is the topical composition of Embodiment 24, wherein the aqueous extracts are in powdered form. Embodiment 27 is the composition of any of Embodiments 20 to 26, wherein the saccharide isomerate comprises an exopolysaccharide of *Vibrio alginolyticus* belonging to the family of Thalasso plankton. Embodiment 28 is the composition of any of Embodiments 20 to 27, wherein the *Myrothamnus flabellifolia* extract is an extract of the leaf and stem of *Myrothamnus flabellifolia*. Embodiment 29 is the composition of any of Embodiments 20 to 28, wherein the *Phoenix dactylifera* extract is a water soluble extract from *Phoenix dactylifera* seeds. Embodiment 30 is the composition of any of Embodiments 20 to 29, wherein the tea tree oil is an essential oil from the leaves of the tea tree *Melaleuca alternifolia*. Embodiment 31 is the composition of any of Embodiments 20 to 30, wherein the topical composition further comprises water. Embodiment 32 is the composition of any of Embodiments 20 to 31, wherein the topical composition is an emulsion, serum, gel, gel emulsion, or gel serum. Embodiment 33 is the composition of any of Embodiments 20 to 32, wherein the topical composition is an oil in water emulsion or water in oil emulsion. Embodiment 34 is the composition of any of Embodiments 20 to 33, wherein the topical composition is formulated to be applied to skin of a face. Embodiment 35 is the composition of any of Embodiments 20 to 34, wherein the topical composition comprises an effective amount of *Phoenix dactylifera* extract to increase α2A adrenergic receptor agonist activity, reduce oxidation, increase anti-oxidant capacity of the composition or of skin, inhibit cyclooxygenase-2 (COX-2) production, inhibit vascular endothelial growth factor (VEGF) production, inhibit interleukin-6 (IL-6) and interleukin-8 (IL-8) production, reduce tumor necrosis factor alpha (TNF-α) production, increase collagen stimulation, increase lysyl oxidase expression, and/or inhibit matrix metalloproteinase 1 (MMP1) activity. Embodiment 36 is the composition of any of Embodiments 20 to 35, wherein the topical composition comprises an effective amount of tea tree oil to kill *Demodex folliculorum* and *Demodex brevis*. Embodiment 37 is the composition of any of Embodiments 20 to 36, wherein the topical composition comprises an effective amount of saccharide isomerate to reduce tumor necrosis factor alpha (TNF-α) production, inhibit nitric oxide synthase, increase occludin production, increase filaggrin production, and/or increase skin moisturization. Embodiment 38 is the composition of any of Embodiments 20 to 37, wherein the topical composition comprises an effective amount of *Myrothamnus flabellifolia* extract to reduce tumor necrosis factor alpha (TNF-α) production, and/or inhibit nitric oxide synthase.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Rosacea" includes, but is not limited to, erythematotelangiectatic rosacea, papulopustular rosacea, phymatous rosacea, and ocular rosacea. Symptoms of rosacea that can be treated by the present invention include, but are not limited to, any one of, a combination of, or all of the following symptoms: redness, transient or persistent flushing of the skin, the appearance of visible blood vessels, particularly in the nose and cheek areas of the face, swelling, swollen red bumps and pimples that can also contain pus, transient or persistent erythema, inflammation, skin thickening, bumpy skin texture, skin dryness, skin irritation, telangiectasia, inflammatory papules and/or pustules, and/or hyperplasia of a connective tissue.

"Keratinous tissue" includes keratin-containing layers disposed as the outermost protective covering of mammals and includes, but is not limited to, lips, skin, hair, and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations refer to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and methods of the present invention is a composition containing *Phoenix dactylifera* extract, tea tree oil, *Myrothamnus flabellifolia* extract, and saccharide isomerate. Another novel property of the compositions and methods is the use of the composition to treat, reduce, and/or prevent completely or in part, rosacea, skin erythema, and/or inflammation, or a symptom or cause thereof.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

As noted above, the present invention provides a solution to the problems associated with rosacea, skin erythema, and/or skin inflammation. The solution is premised on the use of a combination of *Phoenix dactylifera* extract, tea tree oil, *Myrothamnus flabellifolia* extract, and saccharide isomerate to reduce rosacea, skin erythema, and/or skin inflammation. As illustrated in a non-limiting manner in the Examples, this combination has been shown to reduce rosacea, skin erythema, and inflammation, as well as inhibit nitric oxide synthase, increase α2A adrenergic receptor agonist activity, reduce oxidation, inhibit COX-2 production, inhibit VEGF production, inhibit IL-6 production, inhibit IL-8 production, reduce TNF-α production, increase collagen stimulation, increase lysyl oxidase expression, inhibit MMP1 activity, increase occludin production, increase filaggrin production, and/or increase skin moisturization.

These and other non-limiting aspects of the present invention are described in the following sections.

A. Active Ingredients

The present invention is premised on a determination that a combination of active ingredients—*Phoenix dactylifera* extract, tea tree oil, *Myrothamnus flabellifolia* extract, and saccharide isomerate—can be used to reduce rosacea, erythema, and/or inflammation of the skin, as well as inhibit nitric oxide synthase, increase α2A adrenergic receptor agonist activity, reduce oxidation, increase a composition's or skin's anti-oxidant capacity, inhibit COX-2 production, inhibit VEGF production, inhibit IL-6 production, inhibit IL-8 production, reduce TNF-α production, increase collagen stimulation, increase lysyl oxidase expression, inhibit MMP1 activity, increase occludin production, increase filaggrin production, and/or increase skin moisturization.

This combination of ingredients can be used in different products to treat various skin conditions. By way of non-limiting examples, the combination of ingredients can be formulated in an emulsion (e.g. oil-in-water, water-in-oil), a gel, a serum, a gel emulsion, a gel serum, a lotion, a mask, or a body butter.

Saccharide isomerate is an exopolysaccharide synthesized by a micro-organism called *Vibrio alginolyticus* and belonging to the family of Thalasso plankton. In some instances, saccharide isomerate is commercially available. In some instances, saccharide isomerate can be supplied by Barnet Products under the trade name Benoiderm. In some instances, the saccharide isomerate can be provided by extraction from *Vibrio alginolyticus* using an aqueous extraction solvent or an alcohol extraction solvent. In some instances, the extraction solvent can be aqueous. In some instances, the extract can be in liquid form. In some instances, the extract can be in powdered form.

*Myrothamnus flabellifolia* extract is an extract of *Myrothamnus flabellifolia*, also known as the resurrection plant, a flowering plant native to Southern Africa. In some instances, *Myrothamnus flabellifolia* extract is commercially available. In some instances, *Myrothamnus flabellifolia* extract can be supplied by Rahn under the trade name MYRAMAZE®. In some instances, the extract can be an aqueous extract or an alcohol extract. In some instances, the extract can be an aqueous extract. In some instances, the extract is an extract of the whole plant or one or more parts of the plant. In some instances, the extract is an extract of the leaf and stem of the plant. In some instances, the extract can be in liquid form. In some instances, the extract can be in powdered form.

Tea tree oil, also known as *melaleuca* oil or ti tree oil, is an essential oil from the leaves of the tea tree, *Melaleuca alternifolia*. In some instances, tea tree oil is commercially available. In some instances, tea tree oil can be supplied by Southern Cross Botanicals under the trade name MELAFRESH™ T96.

*Phoenix dactylifera* extract is an extract of *Phoenix dactylifera*, also known as date palm, a flowering plant species in the palm family, Arecaceae. In some instances, *Phoenix dactylifera* is commercially available. In some instances, *Phoenix dactylifera* extract can be supplied by IBR Ltd. under the trade name IBR-CALMDEAGE®. In some instances, the extract can be a water soluble extract from palm date seeds. In some instances, the extract can be an aqueous extract or an alcohol extract. In some instances, the extract can be an aqueous extract. In some instances, the extract is an extract of the whole plant or one or more parts of the plant. In some instances, the extract is an extract of the whole plant. In some instances, the extract is an extract of the seeds and/or fruit.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc. In particular instances, the extracts are aqueous extracts.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the ingredients within the compositions can vary. In non-limiting embodiments, for example, the compositions can comprise, consist essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methyl silanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solid.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil having a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); and low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

g. Exfoliating Agents

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several methods known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160 to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

i. Thickening Agents

Thickening agents, including thickener or gelling agents, include substances that can increase the viscosity of a composition. Thickeners include those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerythritol (e.g., CARBOPOL™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids, and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three units.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal, or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

1. Example 1 (Materials Used)

The active ingredients in Table 1 were used to obtain the in vitro data noted below.

TABLE 1

| Ingredient |
| --- |
| Saccharide isomerate, an aqueous extract containing an exopolysaccharide synthesized by a micro-organism called *Vibrio alginolyticus* and belonging to the family of Thalasso plankton-supplied by Barnet Products under the trade name Benoiderm. |
| Aqueous leaf and stem extract of *Myrothamnus flabellifolia*-supplied by Rahn under the trade name MYRAMAZE ®. |
| Tea tree oil, an essential oil from the leaves of the tea tree, *Melaleuca alternifolia*-supplied by Southern Cross Botanicals under the trade name MELAFRESH ™ T96. |
| *Phoenix dactylifera* extract, a water soluble extract from palm date seeds, also known as date palm, a flowering plant species in the palm family, Arecaceae-supplied by IBR Ltd. under the trade name IBR-CALMDEAGE ®. |

2. Example 2 (In-Vitro Studies)

It has been determined that the combination of *Phoenix dactylifera* extract, tea tree oil, *Myrothamnus flabellifolia* extract, and saccharide isomerate can inhibit nitric oxide synthase, increase α2A adrenergic receptor agonist activity, reduce oxidation, increase a composition's or skin's antioxidant capacity, inhibit COX-2 production, inhibit VEGF production, inhibit IL-6 production, inhibit IL-8 production, reduce TNF-α production, increase collagen stimulation, increase lysyl oxidase expression, inhibit MMP1 activity, increase occludin production, increase filaggrin production, and/or increase skin moisturization. A summary of results are found in Table 2, and the methods used to determine the properties of the ingredients are provided below.

metabotropic (i.e., influencing metabolism) G protein-coupled receptors (GPCR). Many types of cells possess these receptors, and the binding of an agonist (activator) will generally cause a sympathetic response, depending on the receptor being affected (e.g., heart rate modification, vasoconstriction/dilation, fat metabolism changes, etc.). An agonistic effect on the α2A adrenergic receptor of smooth muscle cells may result in a vasoconstrictive effect—meaning, the blood vessels in which these cells and receptors are present will constrict and limit the pooling of blood and lymph in the area, which may result in an improved, homogenous appearance of the skin in that area and a reduction of the dark circles and rosacea symptoms.

Cellular dielectric spectroscopy (CDS) is a technique that measures impedance changes caused by activation of the target cellular receptor across a cell culture. CDS was used to determine α2A adrenergic receptor activity in recombinant Chinese hamster ovary (CHO) cells expressing the human α2A receptor. The changes caused by treatment with the embodiments were compared with the effects of a positive control reference activator (100 nM epinephrine), and were expressed as a percentage of the positive control reference's effect ((measured specific response/control specific agonist response)×100). It was shown that *Phoenix dactylifera* extract increased α2A adrenergic receptor ago-

TABLE 2

| Ingredient | Assay | Activity compared to control |
| --- | --- | --- |
| *Phoenix dactylifera* extract (1% IBR-CALMDEAGE ® unless otherwise indicated) | α2A Adrenergic Receptor Agonist Activity @ 0.5% IBR-CALMDEAGE ® | 24% of epinephrine response |
| | α2A Adrenergic Receptor Agonist Activity @ 1.5% IBR-CALMDEAGE ® | 65% of epinephrine response |
| | α2A Adrenergic Receptor Agonist Activity @ 4.5% IBR-CALMDEAGE ® | 102% of epinephrine response |
| | Antioxidant Capacity | 99.25% of Trolox response |
| | COX-2 Activity | −85.02% |
| | IL-6 Production | −73.4% |
| | IL-8 Production | −97.15% |
| | TNF-α Production | −84.6% |
| | VEGF Production | −86.4% |
| | Collagen Stimulation | 25.3% |
| | Lysyl Oxidase Production | 38.37% |
| | MMP-1 Activity | −70.34% |
| Saccharide isomerate (1% Benoiderm) | TNF-α Production | −88% |
| | Nitric Oxide Synthase Activity | −45% |
| | Occludin-1 Production | 100% |
| | Filaggrin Production | 27% |
| *Myrothamnus flabellifolia* extract (1% MYRAMAZE ®) | TNF-α Production | −80% |
| | Nitric Oxide Synthase Activity | −36% |

Alpha-2A Adrenergic Receptor Agonist Assay: *Phoenix dactylifera* extract was shown to increase α2A adrenergic receptor agonist activity. The adrenergic receptors are nist activity, potentially affecting capillary blood vessel constriction and alleviating dark circles and rosacea. Specifically, 0.5% *Phoenix dactylifera* extract increased α2A adrenergic receptor activity by 24% of the positive control response, 1.5% *Phoenix dactylifera* extract increased α2A adrenergic receptor activity by 65% of the positive control response, and 4.5% *Phoenix dactylifera* extract increased α2A adrenergic receptor activity by 102% of the positive control response. See Table 2.

Nitric Oxide Synthase Activity Assay: Saccharide isomerate and *Myrothamnus flabellifolia* extract have been shown to reduce nitric oxide synthase activity. Nitric oxide (NO) is a reactive radical that plays an important role in many key physiological functions. NO is involved in host defense and development, activation of regulatory proteins, and direct covalent interaction with functional biomolecules. NOS is an important mediator of vasodilation in blood vessels. Nitric oxide synthases (NOS) are a family of enzymes catalyzing the production of nitric oxide (NO) from L-arginine. A NOS assay (Abnova, KA1634) was used that included two steps: a NOS reaction step during which NO was produced followed by an NO detection step. Since the NO generated by NOS is rapidly oxidized to nitrite and nitrate, NO production was measured following reduction of nitrate to nitrite using an improved Griess method. This bioassay was used to analyze the effect of saccharide isomerate and *Myrothamnus flabellifolia* extract on the production of NO by NOS. It was shown that saccharide isomerate and *Myrothamnus flabellifolia* extract reduced the activity of NOS greater than the 1 μM SIN-1 positive control. Specifically, the activity of NOS was reduced by approximately 45% by saccharide isomerate and 36% by *Myrothamnus flabellifolia* extract, while the positive control only reduced the activity of NOS by approximately 29% (not shown). See Table 2.

Tumor Necrosis Factor Alpha (TNF-α) Assay: *Phoenix dactylifera* extract, saccharide isomerate, and *Myrothamnus flabellifolia* extract have been shown to inhibit TNF-α production. The prototype ligand of the TNF superfamily, TNF-α, is a pleiotropic cytokine that plays a central role in inflammation. Increase in its expression is associated with an up regulation in pro-inflammatory activity. This bioassay was used to analyze the effect of *Phoenix dactylifera* extract, saccharide isomerate, and *Myrothamnus flabellifolia* extract on the production of TNF-α by human epidermal keratinocytes. The endpoint of this assay was a spectrophotometric measurement that reflects the presence of TNF-α and cellular viability. The assay employed the quantitative sandwich enzyme immunoassay technique whereby a monoclonal antibody specific for TNF-α was pre-coated onto a microplate. Standards and samples were pipetted into the wells, and any TNF-α present was bound by the immobilized antibody. After washing away any unbound substances, an enzyme-linked polyclonal antibody specific for TNF-α was added to the wells. Following a wash to remove any unbound antibody-enzyme reagent, a substrate solution was added to the wells and color developed in proportion to the amount of TNF-α bound in the initial step. The color development was stopped, and the intensity of the color was measured. A microplate reader was used for detection at 450 nm.

Subconfluent normal human adult keratinocytes (Cascade Biologics) cultivated in EPILIFE® standard growth medium (Cascade Biologics) at 37° C. in 5% $CO_2$, were treated with phorbol 12-myristate 13-acetate (PMA, 10 ng/ml, Sigma Chemical, #P1585-1MG) in the presence or absence of the test extracts or controls for 6 hours. PMA causes a dramatic increase in TNF-α secretion which peaks at 6 hours after treatment. Following incubation, cell culture medium was collected and the amount of TNF-α secretion was quantified using the sandwich enzyme linked immuno-sorbant assay (ELISA) from R&D Systems (#DTA00C) described above. It was shown that *Phoenix dactylifera* extract, saccharide isomerate, and *Myrothamnus flabellifolia* extract reduced the production of TNF-α. Specifically, the production of TNF-α was reduced by approximately 84.6% by *Phoenix dactylifera* extract, 88% by saccharide isomerate, and 80% by *Myrothamnus flabellifolia* extract. See Table 2.

Production of Occludin-1: Saccharide isomerate has been shown to increase occludin-1 production in keratinocytes. Occludin-1 is a protein critical to the formulation of tight junctions and the skin's moisture barrier function. Occludin-1 production in treated and non-treated keratinocytes was determined by the use of a bioassay that analyzes occludin-1 concentration in keratinocyte cell lysates. The bioassay was performed using PROTEINSIMPLE® SIMON™ western blotting protocol. For the samples, adult human epidermal keratinocytes (HEKa) from Life Technologies (C-005-5C) were grown at 37° C. and 5% CO2 for 24 hours in EPILIFE® growth media with calcium from Life Technologies (M-EP-500-CA) supplemented with Keratinocyte Growth Supplement (HKGS) from Life Technologies (S-101-5). HEKa cells were then incubated for 24 to 48 hours in growth medium containing test compound, no compound for negative control, or with 1 mM $CaCl_2$ for positive control. The HEKa cells were then washed, collected, and stored on ice or colder until lysed on ice using a lysis buffer and sonication. The protein concentrations of the samples were determined and used to normalize the samples. The lysates were stored at −80° C. until use in the bioassay.

The PROTEINSIMPLE® SIMON™ western blotting bioassay assay employed a quantitative western blotting immunoassay technique using an antibody specific for occludin to quantitatively detect occludin in the test samples. Cell samples were lysed and normalized for protein concentration as described above. Normalized samples and molecular weight standards were loaded and run on a denatured protein separation gel using capillary electrophoresis. The proteins in the gel were then immobilized and immunoprobed using a primary antibody specific for occludin. The immobilized proteins were then immunoprobed with an enzyme-linked detection antibody that binds the primary antibody. A chemiluminescent substrate solution was then added to the immobilized proteins to allow chemiluminescent development in proportion to the amount of occludin bound in the immobilization. The chemiluminescent development was stopped at a specific time, and the intensity of the chemiluminescent signal was measured and compared to positive and negative controls. It was shown that saccharide isomerate increased the production of occludin-1 by 100%. See Table 2.

Production of Filaggrin: Saccharide isomerate has been shown to increase filaggrin production. Filaggrin is the precursor to Natural Moisturizing Factor (NMF) in the skin. Increased NMF increases the moisture content of the skin. Filaggrin production in treated and non-treated keratinocytes was determined using a bioassay that analyzes filaggrin concentration in keratinocyte cell lysates. The PROTEINSIMPLE® Simon™ western blotting protocol was used to quantify filaggrin production. For each sample, normal human epidermal keratinocytes (NHEK) were grown in EPI-200—Mattek EPILIFE® growth media with calcium from Life Technologies (M-EP-500-CA). NHEK cells were incubated in growth medium overnight at 37° C. in 5% $CO_2$ prior to treatment. NHEK cells were then incubated in growth medium with 1% test compound/extract or no compound/extract (negative control) for 24 to 36 hours. The NHEK cells were then washed, collected, and stored on ice or colder until lysed on ice using a lysis buffer and sonication. The protein concentrations of the samples were determined and used to normalize the samples. The lysates were stored at −80° C. until use in the quantification assay.

The PROTEINSIMPLE® Simon™ western blotting bioassay assay employs a quantitative western blotting immunoassay technique using an antibody specific for filaggrin to quantitatively detect filaggrin in the test samples. Cell samples were lysed and normalized for protein concentration. Normalized samples and molecular weight standards were loaded and ran on a denatured protein separation gel using capillary electrophoresis. The proteins in the gel were immobilized and immunoprobed using a primary antibody specific for filaggrin. The immobilized proteins were then immunoprobed with an enzyme-linked detection antibody that binds the primary antibody. A chemiluminescent substrate solution was then added to the immobilized proteins to allow chemiluminescent development in proportion to the amount of filaggrin bound in the immobilization. The chemiluminescent development was stopped at a specific time, and the intensity of the chemiluminescent signal was measured and compared to positive and negative controls. It was shown that saccharide isomerate increased production of filaggrin by 27%. See Table 2.

Moisture/Hydration Assay: Saccharide isomerate was shown to increase a measurement of skin moisturization using a moisture/hydration assay. This assay determined impedance measurements with a Nova Dermal Phase Meter. The impedance meter measured changes in moisture content of tissue engineered, three-dimensional, cultured artificial skin equivalents (MatTek Corporation). The outer layer of the skin has distinct electrical properties. When skin is dry, it conducts electricity very poorly. As it becomes more hydrated, conductivity increases. Consequently, changes in impedance (related to conductivity) were used to assess changes in hydration of the artificial skin equivalents.

For this assay, treated and non-treated artificial skin equivalents were used. The Nova Dermal Phase Meter was calibrated according to instrument instructions for each testing day. A notation of temperature and relative humidity was made for comparison purposes. Impedance was evaluated as follows: prior to measurement, the samples were equilibrated in a room with defined humidity (e.g., 30-50%) and temperature (e.g., 68-72° C.). Impedance readings were taken on each sample, recorded, and averaged. The T5 setting was used on the impedance meter which averages the impedance values of every five seconds after application to the sample. Changes were reported with statistical variance and significance. It was determined that saccharide isomerate increased conductance by 80%, indicating increased moisture/hydration. See Table 2.

Antioxidant (AO) Assay: *Phoenix dactylifera* extract was shown to reduce oxidation of at least one biomarker indicative of total anti-oxidant capacity. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals than any single compound alone. Thus, overall antioxidant capacity may give more relevant biological information compared to that obtained by the measurement of individual components, as it considers the cumulative effect of all antioxidants present in plasma and body fluids. Anti-oxidant capacity kit #709001 from Cayman Chemical (Ann Arbor, Michigan USA) was used as an in vitro bioassay to measure the total anti-oxidant capacity of *Phoenix dactylifera* extract. The assay relies on the ability of antioxidants in test samples to inhibit the oxidation of ABTS® (2,2'-azino-di-[3-ethylbenzothiazoline sulphonate]) to ABTS®+ by metmyoglobin. The capacity of the antioxidants in the test samples to prevent ABTS® oxidation is compared with that of Trolox, a water-soluble tocopherol analogue, and are quantified as molar Trolox equivalents. The protocol can be followed according to manufacturer recommendations. It was determined that *Phoenix dactylifera* extract has an oxidation capacity of 99.25% as compared to Trolox. See Table 2.

Cyclooxygenase (COX) Assay: *Phoenix dactylifera* extract has been shown to inhibit COX-2 production. The COX (ovine) Colorimetric Inhibitor screening assay (#760111, Cayman Chemical) was used to determine cyclooxygenase-1 and -2 (COX-1, -2) inhibition. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. The COX inhibitor screening assay measured the peroxidase component of cyclooxygenases. The peroxidase activity was assayed colorimetrically by monitoring the appearance of oxidized N,N,N',N'-tetramethyl-p-phenylenediamine (TMPD). The inhibitor screening assay includes both COX-1 and COX-2 enzymes in order to screen isozyme-specific inhibitors. According to manufacturer instructions, purified enzyme, heme, and test extracts were mixed in assay buffer and incubated with shaking for 15 minutes at room temperature. Following incubation, arachidonic acid and colorimetric substrate were added to initiate the reaction. Color progression was evaluated by colorimetric plate reading at 590 nm. The percent inhibition of COX-1 or COX-2 activity was calculated and compared to non-treated controls to determine the ability of *Phoenix dactylifera* extract to inhibit the activity of the purified enzymes. It was determined that *Phoenix dactylifera* extract inhibits COX-2 peroxidase activity by 85.02%. See Table 2.

Cytokine array (Includes VEGF, IL-6, and IL-8): *Phoenix dactylifera* extract has been shown to inhibit IL-6, IL-8, and VEGF production. IL-6 and IL-8 are cytokines involved in inflammatory and anti-inflammatory response. IL-6 is an interleukin that acts both as a pro-inflammatory cytokine and an anti-inflammatory myokine. IL-8 is a chemotactic and inflammatory cytokine that acts as a key mediator associated with inflammation. VEGF is a cytokine that stimulates vasculogenesis and angiogenesis and may contribute to inflammation, redness, and rosacea. Inhibition of VEGF, IL-6, and IL-8 production was determined with a protein detection assay using biotinylated antibodies to a variety of cytokines for detection of the antibodies. It was determined that *Phoenix dactylifera* extract inhibits VEGF production by 86.4%, inhibits the expression of IL-6 by 73.4%, and inhibits IL-8 production by 97.15%. See Table 2.

Briefly, human epidermal keratinocytes were cultured to 70-80% confluency. The media in the plate was aspirated and 0.025% trypsin/EDTA was added. When the cells became rounded, the culture dish was gently tapped to release the cells. The trypsin/EDTA containing cells were removed from the culture dish and neutralized. Cells were centrifuged for 5 min. at 180×g. The cells formed a pellet and the supernatant was aspirated. The resulting pellet was resuspended in EPILIFE® media (Cascade Biologics). The cells were seeded in 6-well plates at approximately 10-20% confluency. After the cells became approximately 80% confluent, the media was aspirated and 1.0 ml of EPILIFE®, along with phorbol 13-Myristate 12-acetate ("PMA") (a known inducer of inflammation) and *Phoenix dactylifera* extract dilutions were added to two replicate wells. Test compositions were diluted into a final volume of 1 ml (EPILIFE® Growth Medium). The media was gently swirled to ensure adequate mixing. In addition, 1.0 ml of EPILIFE® was added to the control wells, with and without additional PMA. The plates were then incubated at 37±1° C. and 5.0±1% $CO_2$ for approximately 5 hours after dosing. Following this 5-hour incubation, all media was collected in conical tubes and frozen at −70° C., and the frozen media was subsequently shipped on dry ice.

On the day of the analysis, a 16-pad hybridization chamber was attached to 16-pad FAST slides arrayed in triplicate with 16 anti-cytokine antibodies (including VEGF, IL-6, and IL-8) plus experimental controls (Whatman BioSciences), and the slides were placed into a FAST™ Frame (4 slides per frame) for processing. Arrays were blocked for 15 min. at room temp. using 70 ml S&S Protein Array Blocking buffer (Whatman Schleicher and Scheull). Blocking buffer was removed and 70 ml of each supernatant sample was added to each array. Arrays were incubated for 3 hours at room temp. with gentle agitation. Arrays were washed 3 times with TBS-T. Arrays were treated with 70 ml of an antibody cocktail, containing one biotinylated antibody corresponding to each of the arrayed capture antibodies. Arrays were incubated for 1 hour at room temp. with gentle agitation. Arrays were washed 3 times with tris-buffered saline (TBS-T). Arrays were incubated with 70 ml of a solution containing streptavidin-Cy5 conjugate for 1 hour at room temp. with gentle agitation. Arrays were washed 3 times with TBS-T, quickly rinsed in de-ionized water, and dried.

Slides were imaged in a Perkin-Elmer SCANARRAY® 4000 confocal fluorescent imaging system. Array images were saved and analyzed using Imaging Research ArrayVision software. Briefly, spot intensities were determined by subtracting background signal. Spot replicates from each sample condition were averaged and then compared to the appropriate controls.

Collagen Stimulation Assay: *Phoenix dactylifera* extract has been shown to increase collagen stimulation. Collagen is an extracellular matrix protein critical for skin structure. Increased synthesis of collagen helps improve skin firmness and elasticity. This bioassay was used to examine the effect of *Phoenix dactylifera* extract on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples were pipetted into the wells, and any procollagen peptide present was bound by the immobilized antibody. After washing away any unbound substances, an enzyme-linked polyclonal antibody specific for procollagen peptide was added to the wells. Following a wash to remove any unbound antibody-enzyme reagent, a substrate solution was added to the wells, and color was developed in proportion to the amount of procollagen peptide bound in the initial step. Color development was stopped, and the intensity of the color at 450 nm was measured using a microplate reader.

For generation of samples and controls, subconfluent normal human adult epidermal fibroblasts (Cascade Biologics) were cultivated in standard DMEM growth medium with 10% fetal bovine serum (Mediatech) at 37° C. in 10% $CO_2$. The cells were treated with *Phoenix dactylifera* extract and controls for 3 days. Following incubation, cell culture medium was collected, and the amount of procollagen peptide secretion was quantified using the sandwich enzyme linked immuno-sorbant assay (ELISA) from Takara (#MK101) as explained above. It was determined that *Phoenix dactylifera* extract increased collagen stimulation by 25.3%. See Table 2.

Lysyl Oxidase Assay: *Phoenix dactylifera* extract was shown to increase lysyl oxidase expression. A lysyl oxidase assay was performed on skin cells (e.g., epidermal keratinocytes, fibroblasts, and/or dermal endothelial cells) to determine the ability of *Phoenix dactylifera* extract to stimulate expression of lysyl oxidase in skin. Lysyl oxidase can catalyze crosslinking of elastin and collagens, thereby providing for a more structurally rigid matrix for skin. By increasing expression of lysyl oxidase, increased crosslinking of elastin and collagens can occur, which can be beneficial in reducing the appearance of fine lines, wrinkles, sagging skin, and/or non-elastic skin. It was determined that *Phoenix dactylifera* extract increased lysyl oxidase expression by 38.37%. See Table 2.

Matrix Metalloproteinase 1 Enzyme Activity (MMP1) Assay: *Phoenix dactylifera* extract was shown to inhibit MMP1 activity. MMPs are extracellular proteases that play a role in many normal and disease states by virtue of their broad substrate specificity. MMP1 substrates include collagen IV.

The Invitrogen™ Molecular Probes™ EnzChek™ Gelatinase/Collagenase Assay kit (#E12055) from Invitrogen is designed as an in vitro assay to measure MMP1 enzymatic activity. The kit utilizes a fluorogenic gelatin substrate to detect MMP1 protease activity. The assay relies upon the ability of purified MMP1 enzyme to degrade a fluorogenic gelatin substrate. Once the substrate is specifically cleaved by MMP1, bright green fluorescence is revealed, and fluorescence was monitored using a fluorescent microplate reader. *Phoenix dactylifera* extract was incubated in the presence or absence of the purified enzyme and substrate to determine the protease inhibitor capacity. It was determined that *Phoenix dactylifera* extract inhibited MMP1 activity by 70.34%. See Table 2.

3. Example 3 (Generic Formulations)

Combinations of the active ingredients can be included in a wide-range of topical product formulations for skin and/or hair. Tables 3 and 4 describe generic formulations or skin testing formulations in which an active ingredient can be incorporated into. These formulations can also be used to determine the types of skin benefits that can be attributed to the active ingredient. These formulations are prepared in such a manner that any resulting skin benefit from topical application of the formula to skin can be directly attributed to the active ingredient being tested. In the context of aspects of the present invention, the active ingredient that can be tested can be *Phoenix dactylifera* extract, tea tree oil, *Myrothamnus flabellifolia* extract, and saccharide isomerate, or any combination thereof, or all of such active ingredients, or at least 1, 2, 3, and/or 4 of such active ingredients. It should be recognized that other standard testing vehicles can also be used to determine the skin benefit properties of active ingredient and that the following formulations are non-limiting testing vehicles.

TABLE 3*

| Ingredient | % Concentration (by weight) |
|---|---|
| Phase A | |
| Water | 84.80 |
| Xanthan gum | 0.1 |
| M-paraben | 0.15 |
| P-paraben | 0.1 |
| Citric acid | 0.1 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Active Ingredient** | 2.0 |
| TOTAL | 100 |

*Procedure for making composition: Sprinkle Xanthan gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The active ingredients identified throughout this specification can be incorporated into a composition as the active ingredient. The active ingredients can be individually used or combined in this composition. The concentration ranges of the active ingredients (or combination of active ingredients) can be modified as desired or needed by increasing or decreasing the amount of water.

TABLE 4*

| Ingredient | % Concentration (by weight) |
|---|---|
| Phase A | |
| Water | 78.6 |
| M-paraben | 0.2 |
| P-paraben | 0.1 |
| Na₂ EDTA | 0.1 |
| Shea butter | 4.5 |
| Petrolatum | 4.5 |
| Glycerin | 4.0 |
| Propylene Glycol | 2.0 |
| FINSOLV ® TN | 2.0 |
| Phase B | |
| SEPIGEL ™ 305 | 2.0 |
| Phase C | |
| Active Ingredient ** | 2.0 |
| TOTAL | 100 |

*Add ingredients in phase A to beaker and heat to 70-75° C. while mixing. Subsequently, add the phase B ingredient with phase A and cool to 30° C. with mixing. Subsequently, add phase C ingredient while mixing.
** The active ingredients identified throughout this specification can be incorporated into a composition as the active ingredient. The active ingredients can be individually used or combined in this composition. The concentration ranges of the active ingredients (or combination of active ingredients) can be modified as desired or needed by increasing or decreasing the amount of water.

4. Example 4 (Exemplary Formulations)

The formulations represented in Tables 5-10 are non-limiting examples of the types of formulations that can be prepared in the context of the present invention. Any standard method can be used to prepare such formulations. For instance, simple mixing of the ingredients in a beaker can be used. One should mix such ingredients and add heat as necessary to obtain a homogenous composition. The active ingredients that can be used in the formulations can include *Phoenix dactylifera* extract, tea tree oil, *Myrothamnus fla-bellifolia* extract, and saccharide isomerate, or any combination thereof, or all of such active ingredients, or at least 1, 2, 3, and/or 4 of such active ingredients.

Table 5 includes a non-limiting example of a composition of the present invention. The composition can be formulated into an emulsion (e.g., o/w, w/o, o/w/o, w/o/w, etc.), and the additional ingredients identified throughout the specification can be included into the Table 5 composition (e.g., by adjusting the water content of composition). Further, the concentration ranges of the ingredients identified in Table 5 can vary depending on a desired formulation (e.g., cream, lotion, moisturizer cleanser, etc.).

TABLE 5

| Ingredient | % Concentration (by weight) |
|---|---|
| Water | q.s. |
| Active Ingredient * | 0.1% to 10% |
| Glycerin | 3 to 40% |
| Butylene glycol | 0.0001 to 10% |
| Propylene glycol | 0.0001 to 10% |
| Phenoxyethanol | 0.0001 to 10% |
| Disodium EDTA | 0.0001 to 10% |
| Steareth-20 | 0.0001 to 10% |
| Chlorhexidine Digluconate | 0.0001 to 10% |
| Potassium Sorbate | 0.0001 to 10% |
| Preservative** | 0.0001 to 2% |
| TOTAL | 100 |

* The active ingredients identified throughout this specification can be incorporated into a composition as the active ingredient. The active ingredients can be individually used or combined in this composition. The concentration ranges of the active ingredients (or combination of active ingredients) can be modified as desired or needed by increasing or decreasing the amount of water.
**Any preservative identified in the specification or those known in the art can be used.

Table 6 includes a non-limiting example of a composition of the present invention. The composition can be formulated into an emulsion (e.g., o/w, w/o, o/w/o, w/o/w, etc.), and the additional ingredients identified throughout the specification can be included into the Table 6 composition (e.g., by adjusting the water content of composition). Further, the concentration ranges of the ingredients identified in Table 6 can vary depending on a desired formulation (e.g., cream, lotion, moisturizer cleanser, etc.).

TABLE 6

| Ingredient | % Concentration (by weight) |
|---|---|
| Water | q.s. |
| Active Ingredient* | 0.1% to 10% |
| Dimethicone | 0.0001 to 10% |
| Triethanolamine | 0.0001 to 10% |
| Phenonip | 0.0001 to 10% |
| Betaine | 0.0001 to 10% |
| Disodium EDTA | 0.0001 to 10% |
| Tocopheryl acetate | 0.0001 to 10% |
| PRODEW ® 400 | 0.0001 to 10% |
| Preservative** | 0.0001 to 2% |
| TOTAL | 100 |

*The active ingredients identified throughout this specification can be incorporated into a composition as the active ingredient. The active ingredients can be individually used or combined in this composition. The concentration ranges of the active ingredients (or combination of active ingredients) can be modified as desired or needed by increasing or decreasing the amount of water.
**Any preservative identified in the specification or those known in the art can be used.

Table 7 includes a non-limiting example of a composition of the present invention. The composition can be formulated into an emulsion (e.g., o/w, w/o, o/w/o, w/o/w, etc.), and the additional ingredients identified throughout the specification can be included into the Table 7 composition (e.g., by adjusting the water content of the composition). Further, the concentration ranges of the ingredients identified in Table 7 can vary depending on a desired formulation (e.g., cream, lotion, moisturizer cleanser, etc.). In particular embodiments, the Table 7 composition can be a moisturizer.

TABLE 7

| Ingredient | % Concentration (by weight) |
| --- | --- |
| Water | q.s. |
| Active Ingredient * | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Capric/Caprylic Triglyceride | 0.0001 to 10% |
| LIPEX ™ 205 (Shea Butter) | 0.0001 to 10% |
| Squalane | 0.0001 to 10% |
| Cetyl Alcohol | 0.0001 to 10% |
| Dimethicone | 0.0001 to 10% |
| Ceramide II | 0.0001 to 10% |
| Stearic Acid | 0.0001 to 10% |
| Super Sterol Ester | 0.0001 to 10% |
| ARLACEL ™ 165 | 0.0001 to 10% |
| SIMULGEL ™ 600 | 0.0001 to 10% |
| TOTAL | 100 |

* The active ingredients identified throughout this specification can be incorporated into a composition as the active ingredient. The active ingredients can be individually used or combined in this composition. The concentration ranges of the active ingredients (or combination of active ingredients) can be modified as desired or needed by increasing or decreasing the amount of water.

Table 8 includes a non-limiting example of a composition of the present invention. The composition can be formulated into an emulsion (e.g., o/w, w/o, o/w/o, w/o/w, etc.), and the additional ingredients identified throughout the specification can be included into the Table 8 composition (e.g., by adjusting the water content of composition). Further, the concentration ranges of the ingredients identified in Table 8 can vary depending on a desired formulation (e.g., cream, lotion, moisturizer cleanser, etc.). In particular embodiments, the Table 8 composition can be a moisturizer.

TABLE 8

| Ingredient | % Concentration (by weight) |
| --- | --- |
| Water | q.s. |
| Active Ingredient * | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Petrolatum | 0.0001 to 10% |
| Squalane | 0.0001 to 10% |
| Cetyl Alcohol | 0.0001 to 10% |
| ARLACEL ™ 165 | 0.0001 to 10% |
| Dimethicone | 0.0001 to 10% |
| SIMULGEL ™ 600 | 0.0001 to 10% |
| TOTAL | 100 |

* The active ingredients identified throughout this specification can be incorporated into a composition as the active ingredient. The active ingredients can be individually used or combined in this composition. The concentration ranges of the active ingredients (or combination of active ingredients) can be modified as desired or needed by increasing or decreasing the amount of water.

Table 9 includes a non-limiting example of a composition of the present invention. The composition can be formulated into an emulsion (e.g., o/w, w/o, o/w/o, w/o/w, etc.), and the additional ingredients identified throughout the specification can be included into the Table 9 composition (e.g., by adjusting the water content of the composition). Further, the concentration ranges of the ingredients identified in Table 9 can vary depending on a desired formulation (e.g., cream, lotion, moisturizer cleanser, etc.). In particular embodiments, the Table 9 composition can be a sunscreen lotion.

TABLE 9

| Ingredient | % Concentration (by weight) |
| --- | --- |
| Water | q.s. |
| Active Ingredient * | 0.1% to 10% |
| Xanthan Gum | 0.0001 to 10% |
| Disodium EDTA | 0.0001 to 10% |
| Pentylene Glycol | 0.0001 to 10% |
| Capryl Glycol | 0.0001 to 10% |
| PEMULEN ™ TR-1 | 0.0001 to 10% |
| Triethanolamine | 0.0001 to 10% |
| PVP/Hexadecene Copolymer | 0.0001 to 10% |
| FINSOLV ® TN | 10 to 30% |
| Sorbitan Isostearate | 0.0001 to 10% |
| Sunscreen Ingredient** | 2 to 25% |
| TOTAL | 100 |

* The active ingredients identified throughout this specification can be incorporated into a composition as the active ingredient. The active ingredients can be individually used or combined in this composition. The concentration ranges of the active ingredients (or combination of active ingredients) can be modified as desired or needed by increasing or decreasing the amount of water.
**Sunscreen ingredient can be any sunscreen ingredient, or combination of such ingredients, identified in the specification (e.g., UV absorbing and/or reflecting agents) or known to those of ordinary skill in the art. In one embodiment, the sunscreen ingredient is a combination of zinc oxide and titanium dioxide.

Table 10 includes a non-limiting example of a composition of the present invention. The additional ingredients identified throughout the specification can be included into the Table 10 composition (e.g., by adjusting the water content of the composition). Further, the concentration ranges of the ingredients identified in Table 10 can vary depending on a desired formulation (e.g., cream, lotion, moisturizer cleanser, etc.). In particular embodiments, the Table 10 composition can be a cleanser.

TABLE 10

| Ingredient | % Concentration (by weight) |
| --- | --- |
| Water | q.s. |
| Active Ingredient* | 0.1% to 10% |
| Disodium EDTA | 0.0001 to 10% |
| Citric Acid | 0.0001 to 10% |
| Pentylene Glycol | 0.0001 to 10% |
| Capryl Glycol | 0.0001 to 10% |
| Sodium Methyl Cocoyl Taurate | 10 to 30% |
| Sodium Cocoamphodiacetate | 1 to 10% |
| TOTAL | 100 |

*The active ingredients identified throughout this specification can be incorporated into a composition as the active ingredient. The active ingredients can be individually used or combined in this composition. The concentration ranges of the active ingredients (or combination of active ingredients) can be modified as desired or needed by increasing or decreasing the amount of water.

5. Example 5 (Additional Assays)

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

B16 Pigmentation Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion is measured by absorbance at 405 nm, and cellular viability is quantified.

Elastin Stimulation Assay: Elastin is a connective tissue protein that helps skin resume shape after stretching or contracting. Elastin is also an important load-bearing protein used in places where mechanical energy is required to be stored. Elastin is made by linking many soluble tropoelastin protein molecules in a reaction catalyzed by lysyl oxidase. Elastin secretion and elastin fibers can be monitored in cultured human fibroblasts by staining of cultured human fibroblasts using immunofluorescent antibodies directed against elastin.

Laminin and Fibronectin Stimulation Assay: Laminin and fibronectin are major proteins in the dermal-epidermal junction (DEJ) (also referred to as the basement membrane). The DEJ is located between the dermis and the epidermis which interlock to form fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ. Laminin and fibronectin secretion can be monitored by quantifying laminin and fibronectin in cell supernatants of cultured human fibroblasts treated for 3 days with culture medium with or without 1.0% final concentration of the test ingredient(s). Following incubation, laminin and fibronectin content can be measured using immunofluorescent antibodies directed against each protein in an enzyme linked immuno-sorbant assay (ELISA). Measurements are normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Antioxidant Assay kit (#AOX-2)). The Zen-Bio ORAC Antioxidant Assay kit measures the loss of fluorescein fluorescence over time due to peroxyl-radical formation by the breakdown of AAPH (2,2'-axobis-2-methyl propanimidamide, dihydrochloride). Trolox, a water soluble vitamin E analog, serves as positive control for inhibition fluorescein decay in a dose dependent manner.

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Matrix Metalloproteinase 3 and 9 Enzyme Activity (MMP3; MMP9) Assay: An in vitro matrix metalloprotease (MMP) inhibition assay is disclosed. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5, 6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M-1 cm-1 at pH 6.0 and above 7). The active ingredients, any one of the combination of ingredients, or compositions having said combinations disclosed in the specification can be assayed.

Lipoxygenase (LO) Assay: An in vitro lipoxygenase (LO) inhibition assay is disclosed. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction, and the mixtures can be incubated for an additional 10 min at room temperature. Colorimetric substrate can be added to terminate catalysis, and color progression can be evaluated by fluorescence plate reading at 490 nm. The percent inhibition of lipoxygenase activity can be calculated compared to non-treated controls to determine the ability of each of the active ingredients, any one of the combination of ingredients, or compositions having said combinations disclosed in the specification to inhibit the activity of purified enzyme.

Elastase Assay: EnzChek® Elastase Assay (Kit #E-12056) from Molecular Probes (Eugene, Oregon USA) can be used as an in vitro enzyme inhibition assay for measuring inhibition of elastase activity for each of the active ingredients, any one of the combination of ingredients, or compositions having said combinations disclosed in the specification. The EnzChek® kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide N-methoxysuccinyl-Ala-Ala-Pro-Val-chloromethyl ketone can be used as a selective, collective inhibitor of elastase when utilizing the EnzChek® Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry, and then transilluminated. Darker blotting paper correlates with more sebum secretion while lighter blotting paper correlates with reduced sebum secretion.

Erythema Assay: An assay to measure the reduction of skin redness can be evaluated using a Minolta Chroma Meter. Skin erythema may be induced by applying a 0.2% solution of sodium dodecyl sulfate on the forearm of a subject. The area is protected by an occlusive patch for 24 hours. After 24 hours, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Clarity and Reduction in Freckles and Age Spots Assay: Skin clarity and the reduction in freckles and age spots can be evaluated using a Minolta Chroma Meter. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Chroma Meter. The measurement is a combination of the a*, b, and L values of the Minolta Chroma Meter and is related to skin brightness and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations can be made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations can be made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness, and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry makes use of a small lightweight probe with a relatively blunt tip (4 square mm-contact area). The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gram force (gf) can be applied parallel to the skin surface, and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas from the subjects' face and analyzing the replicas' image using a computer image analysis system. Replicas can be taken from the eye area and the neck area and photographed with a digital camera using a low angle incidence lighting. The digital images can be analyzed with an image processing program, and wrinkles or fine lines can be determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of a replica, a cross-sectional analysis of skin profile can be generated as a two-dimensional curve. This scan can be repeated any number of times along a fixed axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height; Rt which is the maximum vertical distance between the highest peak and lowest trough; and Rz which is the mean peak amplitude minus the mean peak height. Values are given as a calibrated value in mm. Equipment should be standardized prior to each use by scanning metal standards of known values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Keratinocyte Monolayer Permeability: Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in EPILIFE® growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts, and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran, and the keratinocytes are incubated for 4 hours at 37° C. and 5% $CO_2$. During the 4 hour incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected, and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Production of Hyaluronic Acid: Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time, and the intensity of the color at 450 nm can be measured using a microplate reader.

Inhibition of Hyaluronidase Activity: Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm–inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity: Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Endothelial Tube Formation: Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 μg/ml bovine brain extract, 1 μg/ml hydrocortisone, and 1 μg/ml GA-1000 (gentamicin-amphothericin). HUVEC cultures between passage 3 and 8 may be used for all assay experiments.

HUVECs are pre-labeled with fluorescent agent Calcein AM and seeded in an Extracellular Matrix coated 96-well culture plate with their full growth medium. After about four hours of the morphogenesis process, the endothelial capillary tubes should be formed. Then, test agent in designed doses in 50 μl volume is applied to the formed capillary tubule cultures as treatment conditions. The no-treatment controls can be added with vehicle or test agents. One concentration of Sutent, a FDA approved anti-angiogenic drug, can be included as assay performance control. After about six hours of treatment, the endothelial tubule morphology in each well is examined by microscopy, imaged, and the capillary disrupting activities under treatment condition can be quantitatively analyzed. Each test conditions can be conducted in duplicate wells, including controls.

\* \* \*

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Cosmetic Ingredient Dictionary, Third Edition, CTFA, 1982
International Cosmetic Ingredient Dictionary, Fourth edition, CTFA, 1991
International Cosmetic Ingredient Dictionary and Handbook, Tenth Edition, CTFA, 2004
International Cosmetic Ingredient Dictionary and Handbook, Twelfth Edition, CTFA, 2008
U.S. Pat. No. 5,972,993
U.S. Publication No. 2015/0011489
Tighe, et al. (2013), Terpinen-4-ol is the most active ingredient of tea tree oil to kill *Demodex* mites, *Translational Vision Science & Technology*, 2(7), 1-8. DOI: 10.1167/tvst.2.7.2

The invention claimed is:

1. A method of treating a fine line or wrinkle on the skin under a human's eye and/or moisturizing the skin under a human's eye, the method comprising topically applying to the fine line or wrinkle on the skin under the human's eye a composition comprising:
   a *Melaleuca alternifolia* leaf extract;
   a *Myrothamnus flabellifolia* leaf and stem extract;
   a saccharide isomerate;
   caprylic/capric triglyceride;
   glycerin;
   xanthan gum;
   hyaluronic acid; and
   sodium hyaluronate;
   wherein the fine line or wrinkle on the skin under the human's eye is reduced and/or the moisture of the skin under the human's eye is increased.

2. The method of claim 1, wherein the composition reduces oxidation in the skin of the human.

3. The method of claim 1, wherein the composition is an emulsion.

4. The method of claim 3, wherein the emulsion is an oil-in-water emulsion.

5. The method of claim 1, wherein the composition is a cream or lotion.

6. The method of claim 1, wherein the composition is a gel.

7. The method of claim 1, wherein the composition is applied to dry skin under the human's eye, and the composition moisturizes the dry skin under the human's eye.

8. The method of claim 1, wherein the *Melaleuca alternifolia* leaf extract comprises an essential oil.

9. The method of claim 1, wherein the *Myrothamnus flabellifolia* leaf and stem extract reduces tumor necrosis factor alpha (TNF-α) production and/or inhibits nitric oxide synthase in the skin of the human.

10. The method of claim 1, wherein the *Myrothamnus flabellifolia* leaf and stem extract is an aqueous extract.

11. The method of claim 1, wherein the saccharide isomerate reduces tumor necrosis factor alpha (TNF-α) production and/or inhibits nitric oxide synthase in the skin of the human.

12. The method of claim 1, wherein the saccharide isomerate comprises an exopolysaccharide of *Vibrio alginolyticus*.

13. The method of claim 1, wherein the saccharide isomerate is an aqueous extract of *Vibrio alginolyticus*.

14. The method of claim 1, wherein the composition comprises:
   0.0001 wt. % to 10 wt. % of the *Melaleuca alternifolia* leaf extract;
   0.0001 wt. % to 10 wt. % of the *Myrothamnus flabellifolia* leaf and stem extract; and
   0.0001 wt. % to 10 wt. % of the saccharide isomerate.

15. The method of claim 1, wherein the composition comprises at least 50 wt. % water.

16. The method of claim 1, wherein the composition further comprises a moisturizing agent.

17. The method of claim 1, wherein the composition further comprises an emulsifier or surfactant.

18. The method of claim 1, wherein the composition further comprises a ultraviolet light absorption or reflection agent.

19. The method of claim 1, wherein the composition further comprises:
   ascorbic acid;
   hydrogenated vegetable oil; and
   citric acid.

* * * * *